United States Patent [19]

Weiner

[11] Patent Number: 5,523,221

[45] Date of Patent: Jun. 4, 1996

[54] METHOD FOR THE DIRECTIONAL CLONING OF DNA

[75] Inventor: Michael P. Weiner, San Diego, Calif.

[73] Assignee: Stratagene, La Jolla, Calif.

[21] Appl. No.: 78,662

[22] Filed: Jun. 16, 1993

[51] Int. Cl.[6] ............................ C12N 15/11; C12N 15/66
[52] U.S. Cl. .................................... 435/172.3; 435/320.1; 536/27.11
[58] Field of Search .............................. 435/172.3, 320.1, 435/91.1, 91.4, 91.42; 536/27.11

[56] References Cited

PUBLICATIONS

Sambrook, J. et al. (1989). Molecular Cloning: A Laboratory Manual, 2nd Ed., Cas, N.Y.
Kuisper, J. L. et al. (1992), Gene. 112(2) 147–155.

Primary Examiner—Richard A. Schwartz
Assistant Examiner—Douglas Gurian-Sherman
Attorney, Agent, or Firm—Knobbe, Martens, Olson & Bear

[57] ABSTRACT

A method for directionally cloning an insert DNA fragment into a target sequence using differential phosphorylation is disclosed, Monophosphorylated PCR fragments are directionally cloned into a monophosphorylated plasmid, Methods for directionally cloning non-PCR fragments into target DNA sequences are also discussed.

16 Claims, 6 Drawing Sheets

FIG. 1

(A)  ...GCCCGGGCCTGCAGGATCCCGGCATA...
     ...CGGGCCCGGACGTCCTAGGGCCGTAT...

↓ (Srf I Digestion)

(B)  ...GCCC-OH      P-GGGCCTGCAGGATCCCGGGATA...
     ...CGGG-P      OH-CCCGGACGTCCTAGGGCCGTAT...

↓ (CALF ALKALINE PHOSPHATASE)

(C)  ...GCCC-OH     OH-GGGCCTGCAGGATCCCGGGATA...
     ...CGGG-OH     OH-CCCGGACGTCCTAGGGCCGTAT...

↓ (Sma I Digestion)

(D)  ...GCCC-OH   OH-GGGCCTGCAGGATCCC-OH   P-GGGCATA...
     ...CGGG-OH   OH-CCCGGACGTCCTAGGG-P   OH-CCCGTAT...

↓ (ETOH Precipitation)

(E)  ...GCCC-OH    P-GGGCATA...
     ...CGGG-OH   OH-CCCGTAT...

↓ (Add Monophosphorylated Insert DNA)

(F)  ...GCCC-OH   P-GGCCTT-OH    P-GGGCATA...
     ...CGGG-OH   OH-CCGGAA-OH   OH-CCCGTAT...

P$_{\beta Gal}$->

| SacI/ | NotI/ | SmaI SrfI/ | PstI/ | BamHI/ | SmaI NdeI/ | | AscI/ | KpnI/ |

GAGCTCCGGCGGCCGCCC|GGGCTGCAGGATCCC|GGGCATATGTATATCTCCTTGGGCGCGGTACC
CTCGAGGCCGCCGGCGGG|CCCGACGTCCTAGGG|CCCGTATACATATAGAGGAACCCGCGCCATGG
　　　　　　　　　　　　　　　　　　　　　　　　　　　　　　　　　　　****** fMET　　　　　　<−P$_{T7}$

FIG. 2B

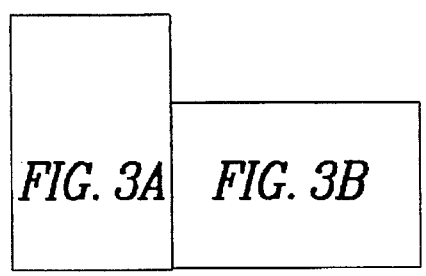
FIG. 3
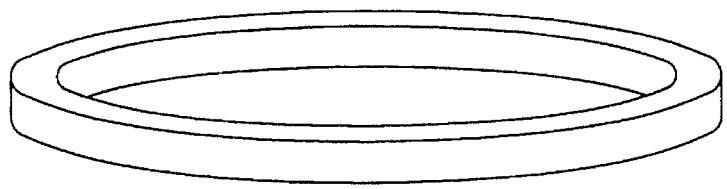
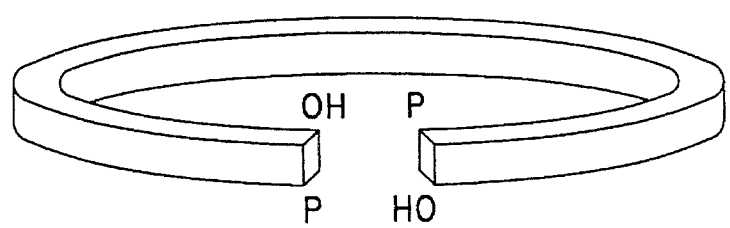
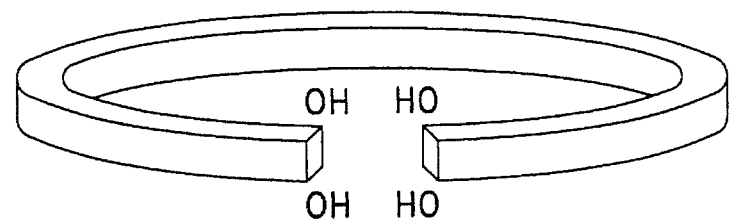
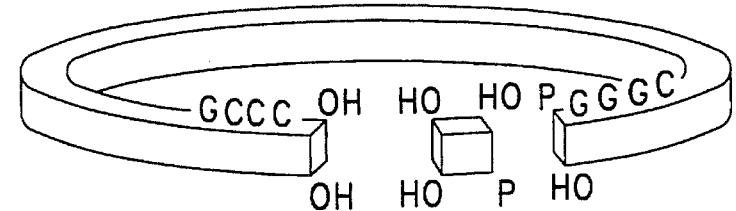
FIG. 3A

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 60
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:1:

```
CCGCGGCCGC  CCGGGCTGCA  GGATCCCGGG  CATATGTATA  TCTCCTTGGC  GCGCCGGTAC      60
```

( 2 ) INFORMATION FOR SEQ ID NO:2:

( i ) SEQUENCE CHARACTERISTICS:
        ( A ) LENGTH: 60
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:2:

```
CGGCGCGCCA  AGGAGATATA  CATATGCCCG  GGATCCTGCA  GCCCGGGCGG  CCGCGGAGCT      60
```

( 2 ) INFORMATION FOR SEQ ID NO:3:

( i ) SEQUENCE CHARACTERISTICS:
        ( A ) LENGTH: 66
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:3:

```
GAGCTCCGCG  GCCGCCCGGG  CTGCAGGATC  CCGGGCATAT  GTATATCTCC  TTGGCGCGCC      60
GGTACC                                                                     66
```

( 2 ) INFORMATION FOR SEQ ID NO:4:

( i ) SEQUENCE CHARACTERISTICS:
        ( A ) LENGTH: 66
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:4:

```
CTCGAGGCGC  CGGCGGGCCC  GACGTCCTAG  GGCCCGTATA  CATATAGAGG  AACCGCGCGG      60
CCATGG                                                                     66
```

( 2 ) INFORMATION FOR SEQ ID NO:5:

( i ) SEQUENCE CHARACTERISTICS:
        ( A ) LENGTH: 16
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:5:

GGGCGGCCGC GGAGCT　　　　　　　　　　　　　　　　　　　　　　　　　　　　　16

( 2 ) INFORMATION FOR SEQ ID NO:6:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:6:

GGGCATATGT TATATCTCCT TGG　　　　　　　　　　　　　　　　　　　　　　　23

( 2 ) INFORMATION FOR SEQ ID NO:7:

( i ) SEQUENCE CHARACTERISTICS:
        ( A ) LENGTH: 20
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:7:

GAAGTCCTTC NNNNAGTACT　　　　　　　　　　　　　　　　　　　　　　　　　20

( 2 ) INFORMATION FOR SEQ ID NO:8:

( i ) SEQUENCE CHARACTERISTICS:
        ( A ) LENGTH: 23
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:8:

CCTGTGACGG AAGATCACTT CGC　　　　　　　　　　　　　　　　　　　　　　　23

( 2 ) INFORMATION FOR SEQ ID NO:9:

( i ) SEQUENCE CHARACTERISTICS:

(A) LENGTH: 22
(B) TYPE: nucleic acid
(C) STRANDEDNESS: double
(D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:9:

CCTCCACGGG GAGAGCCTGA GC         22

(2) INFORMATION FOR SEQ ID NO:10:

(i) SEQUENCE CHARACTERISTICS:
    (A) LENGTH: 27
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:10:

GCCCGGGCCT GCAGGATCCC GGGCATA         27

(2) INFORMATION FOR SEQ ID NO:11:

(i) SEQUENCE CHARACTERISTICS:
    (A) LENGTH: 10
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:11:

GAANNNNTTC         10

(2) INFORMATION FOR SEQ ID NO:12:

(i) SEQUENCE CHARACTERISTICS:
    (A) LENGTH: 10
    (B) TYPE: nucleic acid
    (C) STRANDEDNESS: double
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:12:

GAAGTCCTTC         10

(2) INFORMATION FOR SEQ ID NO:13:

(i) SEQUENCE CHARACTERISTICS:
    (A) LENGTH: 15
    (B) TYPE: nucleic acid
    (C) STRANDEDNESS: double
    (D) TOPOLOGY: linear ( i i ) MOLECULE TYPE: cDNA to mRNA ( i i i ) HYPOTHETICAL: NO ( i v ) ANTI-SENSE: NO ( x i ) SEQUENCE DESCRIPTION: SEQ ID NO:13:

GCCCGGGCCC CGGGC 15

METHOD FOR THE DIRECTIONAL CLONING OF DNA

BACKGROUND OF THE INVENTION

Recombinant DNA technology encompasses many methods for digesting and religating DNA fragments. One of the most widely known uses for recombinant DNA technology is insertion of new genes into target DNA fragments. During this procedure, the target fragment is typically digested with a restriction enzyme, such as EcoRI. Similarly, the insert DNA, having the gene of interest, is digested with the same enzyme. In one type of restriction enzyme digestion, cleavage of both the target DNA and insert DNA leaves overlapping 3' or 5' nucleotide fragments on each end. These overlapping fragments or "sticky ends" are well known properties of some restriction enzymes.

Incubation of the target and insert DNA together at an appropriate temperature allows the insert DNA to noncovalently bind to the target DNA. The target DNA and insert DNA are held together by hydrogen bonding of the "sticky ends". Further incubation with an enzyme, such as DNA ligase, results in ligation of the insert DNA to the target nucleotide strand.

Additional methods of directly cloning DNA fragments into target DNA sequences are available. One such method is described by Mead et al. (*Bio/Technology* (1991) 9:657). This method relies on the ability of Taq polymerase to inherently add deoxyadenosine (dATP) to the 3' end of some newly synthesized duplex molecules described in Clark, J. M. (1988) *Nucleic Acids Research* 20:9677. These single adenosine overhangs base pair with 3' thymidine (dTTP) overhangs at the insertion site of a specially designed vector. It has been found that even single base pairs are sufficient for hydrogen bonding two nucleotide sequences together.

Another method of adding an insert nucleotide fragment into a target DNA is known as blunt-end ligation. Digestion with some restriction enzymes, such as SrfI (GCCC/GGGC), SmaI (CCC/GGG), or Eco RV (GAT/ATC) do not leave any 3' or 5' overhanging nucleotides at the enzyme splice site. These enzymes are known as "blunt-end" enzymes due to this feature of their enzymatic activity. After digestion, blunt-end restriction enzymes maintain single 5' "terminal" phosphates on both sides of the restriction site. These terminal 5' phosphates are required by DNA ligase for any subsequent religation of the digested DNA sequence.

During ligation, DNA ligase covalently links hydrogen bonded double stranded DNA molecules. This enzyme requires a 5' terminal phosphate to act as an electron acceptor. This mechanism is explained in more detail below.

Synthesis of the phosphodiester bond between the 3' hydroxyl group of one nucleotidyl residue and the 5' phosphate ester of the adjacent group occurs in three stages. First, an adenylyl-enzyme intermediate forms. Either ATP or Nicotinamide Adenine Dinucleotide (NAD) can be the source of the adenylyl group. A covalent bond forms between an epsilon-amino group of a ligaselysyl residue and the phosphoryl group of AMP. Second, the 5'-terminal phosphate group of the DNA displaces ligase, resulting in an ADP-DNA adduct. Third, nucleophilic displacement by the same strand 3' hydroxyl group yields the final phosphodiester bond.

Knowledge of this phosphodiester bond synthesis mechanism is used by those with skill in the art. For instance, well known recombinant DNA techniques include the step of dephosphorylating a plasmid following restriction enzyme digestion to prevent religation of the cleaved ends (Sambrook et al. (1989) Molecular Cloning, A laboratory Manual; 2nd Ed. pp. 572 Cold Spring Harbor Laboratory; Cold Spring Harbor, N.Y.). In this method, the insert DNA sequence is cleaved leaving 5'-terminal phosphates on both sides of the restriction site. The target DNA sequence is then dephosphorylated with alkaline phosphatase, thereby being unable to religate due to its lack of 5' phosphates. If an insert DNA is added to this plasmid sample, it can hydrogen bond and ligate to the target due to its 5'-terminal phosphates.

Unfortunately, none of the aforementioned methods permit a researcher to choose a specific orientation for the inserted gene. This presents a distinct disadvantage in that the insert DNA can position itself in either of two 5'-3' orientations with respect to the target nucleotide sequence. Whereas in some instances the insert DNA orientation is unimportant, it is essential in certain procedures, such as ligating a gene to a promoter sequence for obtaining subsequent gene expression.

Following ligation of promoter and gene sequences, genes that are positioned in the wrong 5'→3' orientation will not transcribe a proper protein. Without any directionality provided for the insert, up to 50% of the genes, on average, will insert and ligate in the wrong orientation. This leads to a dramatic reduction in overall experimental efficiency. For this reason, many methods have been devised for preferentially cloning insert DNA fragments into target sequences in one orientation. These methods are commonly known as directional cloning techniques.

Initially, directional cloning was performed by digesting the target nucleotide sequences with two different restriction enzymes. This method resulted in a molecule with dissimilar DNA ends at the target insertion site. The insert DNA would then also be digested with the same two restriction enzymes thereby having two dissimilar DNA ends that corresponded to a specific orientation in the target insertion site. By following this procedure, the insert DNA could only bind the target sequence in one orientation.

Although this method has been widely used in the art, it does present drawbacks. For instance, digesting both the target DNA and insert DNA with multiple restriction enzymes is very time consuming. In addition, multiple enzyme digestions increase the risk that either the target or insert DNA sequence will be cleaved at an internal restriction site. Also, there are problems associated with digesting the ends of DNA strands, such as that required in cutting the insert sequence. Other problems in digesting DNA with two restriction endonucleases include having to change buffers between each reaction. This decreases the probability of properly cutting the DNA.

As discussed above, many investigators have attempted to improve methods relating to directionally cloning of DNA fragments. One of the most widely used procedures involving directional ligation relates to subcloning DNA fragments that have been amplified by the polymerase chain reaction (PCR).

PCR is a technique for amplifying specific regions of DNA by repeated rounds of synthesis and denaturing. In the first step of the technique primers are designed which flank the region to be amplified. A sample of the DNA sequence, in the presence of a molar excess of primers, is repeatedly incubated with polymerase and then the strands denatured. Following denaturation, a primer anneals the newly synthesized strands and the polymerization is repeated. This method leads to an exponential growth in the number of gene sequences.

In the past, directional cloning of PCR amplified DNA involved designing primers with specific internal restriction sites. The PCR fragments generated by these reactions would have primers on either end. Each primer contained its own cleavage sites. For example, following PCR amplification on the DNA of interest, the fragment is digested with two different restriction enzymes. This method leaves a PCR fragment with different restriction sites on each end. The fragment can then be specifically oriented in the target DNA sequence. However, this protocol has the same drawbacks as the aforementioned double digestion method. In addition, the PCR primers have more bases to accommodate the restriction site. This results in added expense for PCR primers.

Another method of directionally cloning an insert into a target sequence uses Exonuclease III (Kaluz, et al., *Nucleic Acids Research*, 20:16, pp. 4369–4370) to create the "sticky ends". In the method described by Kaluz et al., insert DNA fragments were digested with Exonuclease III. The number of nucleotides that Exonuclease III digests from the 3' end of DNA in a minute is well known. After a timed digestion, the insert fragments were left with 5' overlapping nucleotide tails. These tails were engineered so that the 5' ends would only hybridize in one orientation upon base pairing to the target plasmid DNA molecule.

However, the Exonuclease III method is very time dependent and enzyme continues to digest DNA as long as the reaction is incubated. For this reason, Exonuclease III might potentially digest through the end nucleotides and into the coding region of the insert DNA sequence, prompting an unwanted experimental result.

Another method uses the 3' exonuclease activity of T4 DNA polymerase to produce the sticky ends (Kuijper, J. L., et al. (1992) *Gene* 112:147–155.) One further method of directionally cloning PCR generated fragments into a target DNA sequence relies on incorporation of uracil into the PCR primers, followed by treatment with uracil-N-glycosylase (Nisson, P. C., et al. (1991) *PCR Methods and Applications* 1:120–123). The CLONEAMP® SYSTEM (Life Technologies Research Catalog (1992), Gaithersburg, Md.) utilizes uracil DNA glycosylase (UDG) to provide a method of directly cloning PCR fragments into a specially designed plasmid. PCR primers having internal deoxyuracil monophosphate (dUMP) nucleotides are used as primers to amplify the desired gene sequence. After PCR amplification, the sample is treated with UDG to remove the internal dUMP nucleotides. This enzymatic reaction leaves in 3'-overhangs on both ends of the PCR fragment. The fragment is then mixed with a vector having complementary "sticky ends" and ligated. Unfortunately, this method can be difficult to perform since it relies on specially designed dUMP primers for every reaction.

All of the above directional cloning methods require multiple restriction enzyme digestion, addition of extra nucleotides to the insert, or are expensive. For these reasons, there continues to exist a need for a simple, efficient, inexpensive method of directionally cloning a DNA fragment into its target sequence.

SUMMARY OF THE INVENTION

In accordance with the present invention, a method is provided for directionally cloning an insert DNA sequence into a target DNA sequence. This method includes generating a monophosphorylated target DNA sequence, generating a monophosphorylated insert DNA sequence, and then combining the insert DNA sequence, preferably with DNA ligase, with the target sequence, wherein the insert sequence can only ligate in one orientation with respect to the target sequence. Preferably, the target DNA sequence is a plasmid, and more preferably a lambda phage. Advantageously, the target sequence can be produced using calf intestinal alkaline phosphatase (CIAP).

Another embodiment of the present invention is a method for directionally cloning a PCR generated DNA fragment into a target DNA comprising first generating a PCR fragment having only one phosphorylated 5' end. After generating the PCR fragment, a target DNA sequence is digested with a blunt-end restriction enzyme. The next step of the method involves dephosphorylating the 5' ends of the target sequence and then cleaving the target sequence to expose one 5' phosphate. Following cleavage of the target sequence, the PCR generated DNA fragments are ligated with the target sequence, wherein the PCR generated DNA sequence can only ligate in one orientation with respect to the target sequence to generate a covalently closed circular molecule. More preferably, the target DNA sequence is a plasmid, advantageously an expression plasmid. In addition, the dephosphorylating step preferably uses calf intestinal alkaline phosphatase (CIAP). Also, the blunt-end restriction enzyme is preferably SrfI, and the cleaving step uses the Sma I restriction enzyme. Alternatively, the generating step relies on PCR amplification of the insert DNA sequence by using one 5-phosphorylated primer and one unphosphorylated primer.

BRIEF DESCRIPTION OF THE FIGURES

FIG. 1 is a diagram illustrating one preferred method of directionally cloning an insert DNA into a target sequence SEQ ID NO. by the present invention method.

FIGS. 3A and 3B are diagrams of the present invention method for directional cloning. As illustrated, plasmid pMW239 is digested with the restriction enzyme Srf I, treated with CIAP and the alkaline phosphatase removed by phenol/chloroform extraction. The nonphosphorylated plasmid is then restricted with Sma I and ethanol precipitated to remove the 15 bp spacer region. The uniterminally phosphorylated vector is subsequently added to the PCR fragment containing a single 5' phosphate.

DETAILED DESCRIPTION

Figure 2A:
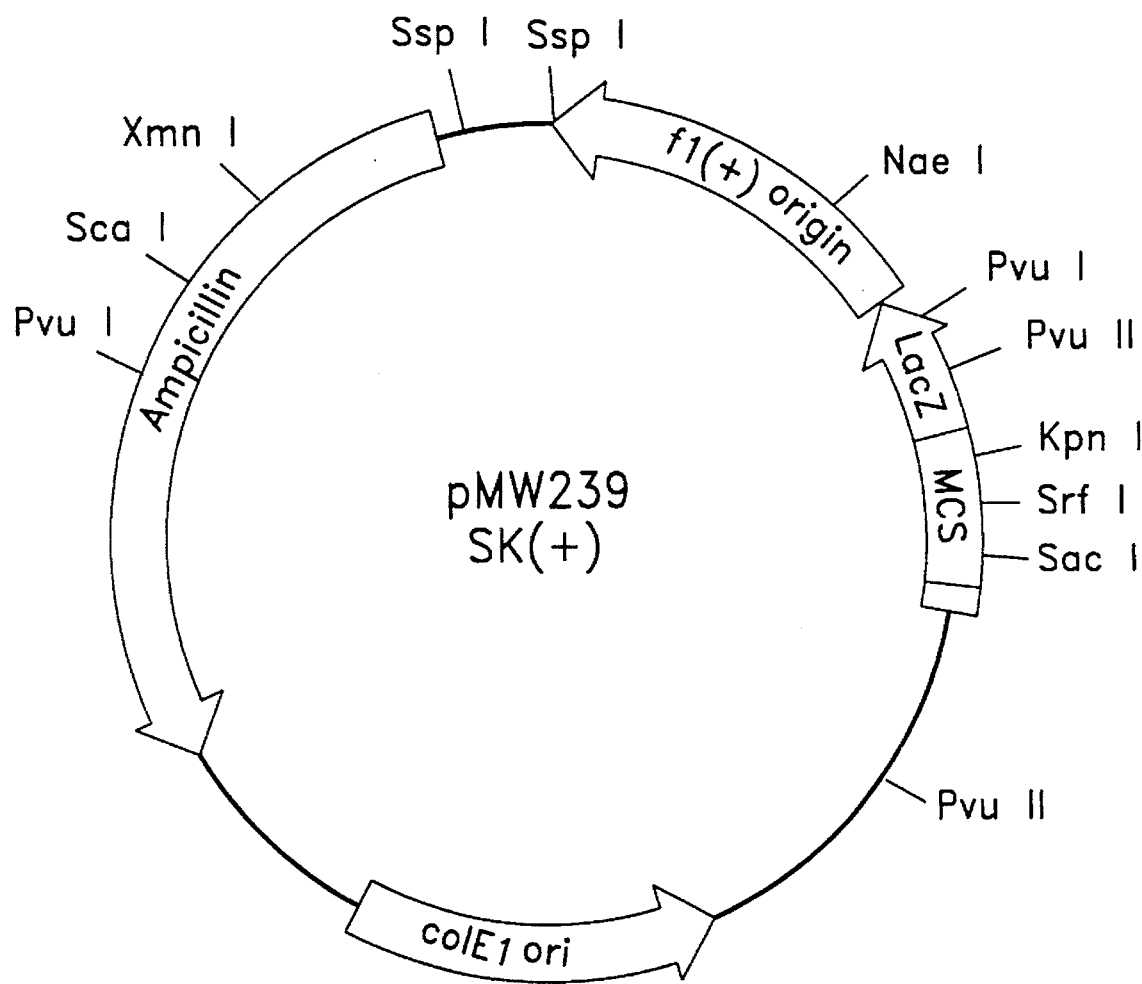
FIG. 2 is a diagram of Plasmid pMW239. This figure illustrates the multiple cloning site; including the ribosome binding site (RBS) and fMET initiation codon for expression of genes from the T7 RNA polymerase binding site in the orientation opposite to that of the b-galactosidase promotor. The region removed by digestion with both Srf I and Sma I is shown in bold. Promotor direction is indicated by the arrow (←) for Pbgal and PT7; RBS, Ribosome binding site; fMET, methionine start codon.

The present invention comprises a method for directionally cloning an insert DNA sequence into its target DNA. This method relies on differential phosphorylation of the insert and target DNA sequences to provide the directional cloning means. In practicing the present invention method, only one 5' end on the insert, and one 5' end on the target are phosphorylated. Following hydrogen bonding, the insert DNA sequence ligates to its target sequence in only one orientation, due to the monophosphorylation of both DNAs. This feature will become more apparent by the explanation of FIG. 1 that follows.

FIG. 1 is a schematic representation of a preferred method for directionally cloning an insert DNA into a target sequence using differential phosphorylation. At Step A, the target DNA sequence (SEQ ID NO. 70) is digested with the blunt-end restriction enzyme Srf I to produce two DNA fragments having the sequences of nucleotides 1–4 and 5–27 of SEQ ID NO:10. As illustrated in Step B, both terminal 5'-phosphates of the target DNA at the restriction site are present. The target sequence is then treated with calf intestine alkaline phosphatase (CIAP) to remove the 5'-phosphates from the splice site of the DNA fragments having the sequences of nucleotides 1–4 and 5–27 of SEQ ID NO:10. As now illustrated in Step C, the 5'-phosphates have been removed resulting in a dephosphorylated splice junction.

To produce the desired monophosphorylated insert site, the target DNA is digested with an additional restriction enzyme, such as Sma I. As illustrated in Step D of FIG. 1, Sma I digestion removes a 15 base pair sequence (nucleotides 5–20 of SEQ ID NO:10) from one end of the target molecule exposing a 5'-phosphate. In Steps D and E the target molecule has two blunt-ends, but only a single phosphate on side of the splice site. It should be appreciated by one skilled in the art that removal of 15 bases from the target sequence conserves the reading frame of the reporter gene, in this case the beta-galactosidase gene of the plasmid.

A monophosphorylated insert DNA, such as that illustrated in Step F, is only able to ligate with the target DNA sequence in one orientation due to the specificity of DNA ligase. It can be appreciated that if the target DNA sequence in Step F attempted to ligate in the opposite orientation, one portion of the splice site would be without a phosphate group and therefore unable to ligate; the result would be a linear plasmid.

It should also be appreciated that there are many alternative methods for producing a monophosphorylated insert or target DNA molecule. For example, the enzyme polynucleotide kinase is used by those with skill in the art to add phosphate groups to the 5'-end of DNA molecules. This enzyme, therefore, could be used to monophosphorylate the splice junction.

In one preferred method of producing a monophosphorylated vector, DNA is first dephosphorylated as illustrated in Steps A, B and C of FIG. 1. During these steps the DNA is cleaved into two fragments. One of the DNA fragments is isolated from the remaining DNA by well known methods, such as gel filtration. After isolation, the DNA is phosphorylated with polynucleotide kinase and then introduced back into the mixture. In this way, only one side of the restriction splice site has a 5'-phosphate, similar to that shown in Step E of FIG. 1.

It should also be recognized that many additional methods for producing monophosphorylated insert and target DNAs are known to those with skill in the art. One preferred method of producing monophosphorylated DNA molecules is related to the method disclosed in FIG. 1. The insert DNA is first treated with calf alkaline phosphatase to remove any 5'-phosphate groups. The insert is then treated with a restriction enzyme designed to cleave the insert very near the end chosen to have the exposed 5'-phosphate group. Ideally, this digestion cleaves a few nucleotides from one end of the DNA strand and exposes a 5'-phosphate. By this method, the insert DNA will be phosphorylated on one end while remain dephosphorylated on the other end.

It can be appreciated that the non-phosphorylated end of the target sequence and the non-phosphorylated end of the insert DNA are unable to ligate due to the lack of a 5'-phosphate required by DNA ligase. Only one potential orientation for insert target ligation is thereby available. Proper orientation occurs when the 5'-phosphorylated end of the insert DNA molecule aligns with the non-phosphorylated 3' end of the target DNA. By using these properties of DNA biochemistry, the present invention advantageously promotes directional cloning of DNA fragments.

Further, it is well known to those with skill in the art that recombinant clones with linker DNA have reduced E. coli transfection efficiencies. The cloning method of the present invention is therefore advantageous since the method does not require insertion of DNA linkers. For this reason, transfection efficiencies of clones produced by the present invention method are greater than other techniques requiring the use of DNA linkers.

As discussed below, the preferred method of practicing the present invention relates to directionally cloning PCR fragments into cloning vectors. Although this is the preferred embodiment, one of ordinary skill in the art can readily appreciate that the present method can be performed to unidirectionally clone any insert DNA sequence into a target DNA sequence. Accordingly, alternative methods of directionally cloning a monophosphorylated or monohydroxylated insert DNA sequence into a monophosphorylated or monohydroxylated target DNA sequence are anticipated to be within the scope of the present invention.

DESCRIPTION OF THE PREFERRED EMBODIMENT

In the preferred embodiment of the present invention, the inventive method is used to directionally clone PCR fragments into their target DNA sequences. As explained in more detail below, two PCR primers are used to produce the desired PCR fragments. One primer has a 5'-phosphate, while the other primer is unphosphorylated. After PCR amplification, the resultant DNA fragments have one 5' phosphorylated end and one non-phosphorylated end.

To provide the inventive directionality in this cloning technique, the target vector is engineered to be monophosphorylated at the insertion site. This method proceeds similarly to that discussed in regard to FIG. 1 above. In the preferred embodiment, the circular plasmid was first cleaved with a blunt-end restriction enzyme leaving two phosphorylated 5' ends. The plasmid is then treated with calf intestinal alkaline phosphatase (CIAP) to remove both 5'-phosphates. Following this step, the target vector is cleaved with an additional blunt-end enzyme to expose a 5'-phosphate on only one side of the restriction site. The plasmid now has one end with a 5' phosphate and one unphosphorylated end. As discussed above, the insert DNA fragment and the target vector are now able to ligate in only one orientation.

It can be appreciated that the scope of the present invention includes any methods wherein a differential phosphorylation provides the means for directional cloning of two or more DNA fragments. The following describes the preferred method of the present invention.

METHODS

Enzymes

Srf I, Sma I, Sca I, Sac I, KpnI, T4 DNA ligase, Calf intestinal alkaline phosphatase (CIAP) and 10X Universal buffer were obtained from Stratagene (La Jolla, Calif.). All enzymatic reactions (Srf I, Sma I, Sac I and Kpn I, CIAP, and T4 DNA ligase) were performed in 1X Universal buffer (Stratagene), T4 DNA ligase reactions contained 0.5 mM ATP (final).

Media

Luria-Bertani (LB) medium contained tryptone (10 g l-1), yeast extract (5 g l-1), and NaCl (10 g l-1). LB plates were supplemented with ampicillin and methicillin at 20 mg and 80 mg per liter, respectively, for b-lactamase resistance, and at 30 mg per liter for chloramphenicol resistance.

Plasmid purification

Large-scale (3 l) plasmid DNA was purified by the alkaline lysis method (3). Mini-prep plasmid DNA was purified by the boiling method (6).

Creation of pMW239

Plasmid pBlueScript II SK(+) (Stratagene, La Jolla, Calif.) was restricted with Sac I and Kpn I and ligated to annealed primers MW846 and MW847 (listed below) in a vector concentration of 100 ng/μl and annealed oligonucleotide concentration of 0.1 ng/μl.

5'-CCGCGGCCGCCCGGGCTGCAGGATCCCGG GCATATG TATATCTCCTTGGCGCGCCGGTAC-3' SEQUENCE ID NO:1 (MW846)

5'-CGGCGCGCCAAGGAGATATACATATGC- CCGGGATCCTGCAGCCCGGGCGGCCGCG- GAGCT-3' SEQUENCE ID NO:2 (MW847)

The ligation reaction was transformed into XL1Blue (Stratagene) and plated onto LB+Meth/Amp. Blue colonies on Xgal+IPTG-containing LB+Meth/Amp plates after overnight incubation at 37° C. were isolated and several sequenced. A colony with the correct multiple cloning site DNA sequence was labeled pMW239 and chosen for all further experimentation. Table I illustrates the cloning sites in the plasmid pMW239 resuspended to 50 ng/μl in TE (10 mM Tris, pH 7.5, 1 mM EDTA).

Alternative methods of producing monophosphorylated vectors are also anticipated. For example, Polymerase chain reaction (PCR) primers are used to generate the monophosphorylated vector using a thermal stable polymerase such as Taq DNA polymerase. The DNA oligonucleotide primers 5'-pGGGCGGCCGCGGAGCT-3' (SEQ ID NO:5) and 5'-GGGCATATGTTATATCTCCTTGG-3' (SEQ ID NO:6) are placed in a PCR solution containing 1X buffer, dNTPs, 1–10 ng template (pMW239) and DNA polymerase. Importantly, only one of the primers is phosphorylated. After the polymerase chain reaction has gone to completion, the product in solution will be equivalent to a monophosphorylated vector which can be used for unidirectional PCR cloning. By using the above-indicated primers, addition of SrfI in the ligation solution will reduce nonrecombinant background by specifically digesting religated vector DNA, but not cleaving vectors having inserts. By using one phosphorylated and one non-phosphorylated PCR primer in a PCR to generate the vector, any bunt-ended restriction enzyme could be used.

Another method of producing a monophosphorylated vector involves digestion with one or two degenerate restriction enzymes and an alkaline phosphatase. Similar to the method described above, pMW239 is treated with one or more degenerate restriction enzymes to create blunt-ended sites. For instance, a XmnI restriction enzyme site (5'GAANN/NNTTC- 3'; SEQ ID NO:11) can be modified by well known methods to be GAAGT/CCTTC SEQ ID NO:12 whereby restriction with XmnI generates a blunt-ended sequence with one end bearing GAAGT. A second site in the plasmid is generated to be ScaI (AGT/ACT). Treatment of a multiple cloning site having the sequence GAAGT/CCT- TCNNNNAGT/ACT- (SEQ ID NO:7) with XmnI, alkaline phosphatase and ScaI yields a monophosphorylated vector.

TABLE 1 pMW239 SK (+) Multiple Cloning Site

| PbGal → | | | SmaI | | SmaI | | | |
|---|---|---|---|---|---|---|---|---|
| SacI / | | NotI / | | SrfI / | PstI | / | BamHI | / |
| NdeI/ | AscI | / | KpnI | | | | | |

GAGCTCCGCGGCCGCCC GGGCTGCAGGATCCC GGGCATATGTATATCTCCTTGGCGCGCCGTACC (SEQ ID NO: 3)
CTCGAGGCGCCGGCGGG CCCGACGTCCTAGGG CCCGTATACATATAGAGGAACCGCGCGGCCATGG (SEQ ID NO: 4)
                                    fMET   RBS   ← PT7

Example 1: Preparation of monophgsphorylated vector DNA

Twenty μg of plasmid pMW239 at 0.5 μg/μl was digested with 40 units of Srf I for 1 hour at 37° C. Following the digestion, 0.2 units of Calf Intestinal Alkaline Phosphatase (CIAP) were added and the plasmid incubated for an additional 30 minutes at 37° C. The plasmid DNA was extracted twice with Tris-buffered phenol and twice with CHCl₃. The dephosphorylated plasmid DNA was incubated for 20 minutes at 70° C. and then cooled on ice.

The plasmid was then diluted to 0.1 μg/μl with 1x Universal buffer followed by digestion with 40 units of Sma I to reveal a 5'-phosphate on one side of the Srf I splice site. The restriction digestion continued for 1 h at 34° C. The restriction endonuclease was heat-killed for 20 minutes at 70° C. The monophosphorylated CIAP/restriction endonuclease-treated plasmid DNA was precipitated with 0.1 volumes of 10 M LiCl and 2.5 volumes of ice-cold ethanol. The plasmid was centrifuged in an Eppendorf® tube at 15,000 rpm and vacuum dried. The monophosphorylated vector was In this case, use of ScaI in the ligation solution reduces nonrecombinant background by digesting religated vector DNA, and not digesting vectors into which an insert has been cloned.

Now that a monophosphorylated vector had been prepared, we produced monophosphorylated insert DNA by the PCR method as described below.

Experiment 2: PCR protocol

The chloramphenicol gene from plasmid pBC SK(−) (Stratagene, La Jolla, Calif.) was amplified by PCR using the flanking oligonucleotide primers MW227 and MW228 shown below:

MW227 5'-CCTGTGACGGAAGATCACTTCGC-3'
                                    (SEQ ID NO: 8)
MW228 5' CCTCCA CGGGGAGAGCCTGAGC-3'
                                    (SEQ ID NO: 9)

MW228 was synthesized with a 5'-terminal phosphate while MW227 was nonphosphorylated. The PCR was performed with, per 100 μl, 1 μg of each primer, 50 nM dNTP, 100 ng template DNA (restriction endonuclease Pst I-digested pBC SK+ DNA) and 10 units of Taq DNA polymerase in 1X Taq polymerase buffer. PCR cycle conditions were 1 minute at 54° C., 1 minute at 72° C., 1 minute at 90° C. for 40 cycles, followed by 10 minutes at 72° C.

Following PCR amplification of the insert DNA we ligated the insert to the monophosphorylated target as described in the following example.

Example 3: Ligation procedure and transformation

The ligation reactions were performed in 10 μl of 1x universal buffer containing 50 ng plasmid DNA, 200 ng PCR product, 500 nM ATP, 4 Units T4 DNA ligase and 15 Units of Srf I. The reaction was incubated for 1 h at room temperature and then heated for 10 minutes at 70° C. *E. coli* strain XL1Blue (100 μl, Stratagene) was transformed with 2 μl of the ligation reaction and plated onto LB+Meth/Amp+IPTG+Xgal. The plates were incubated at 37° C. overnight and phenotypically β-gal colonies were passaged onto LB+chloramphenicol plates. Colonies that were chloramphenicol resistant were inoculated into 20 ml of LB+ampicillin and incubated overnight. Following incubation, the plasmids were isolated by standard mini-preparation protocols.

Liu and Schwartz (*Biotechniques* (1992) 12:28–30) and Bauer et al. (*Strategies in Molecular Biology* (1992) 5:56–58) have shown that incubation of a ligation reaction in the presence of an excess amount of restriction enzyme dramatically increases the yield and efficiency of recombinant plasmid formation. Presumably, this is due to a high steady-state concentration of linearized plasmid DNA in solution that is able to interact with an insert. Religation of vector DNA without insert recreates a restriction target site. In preliminary experiments we were able to optimize the restriction/ligation reaction for approximately 80% completion in 1 hour at room temperature (unpublished results).

Figure 3B:
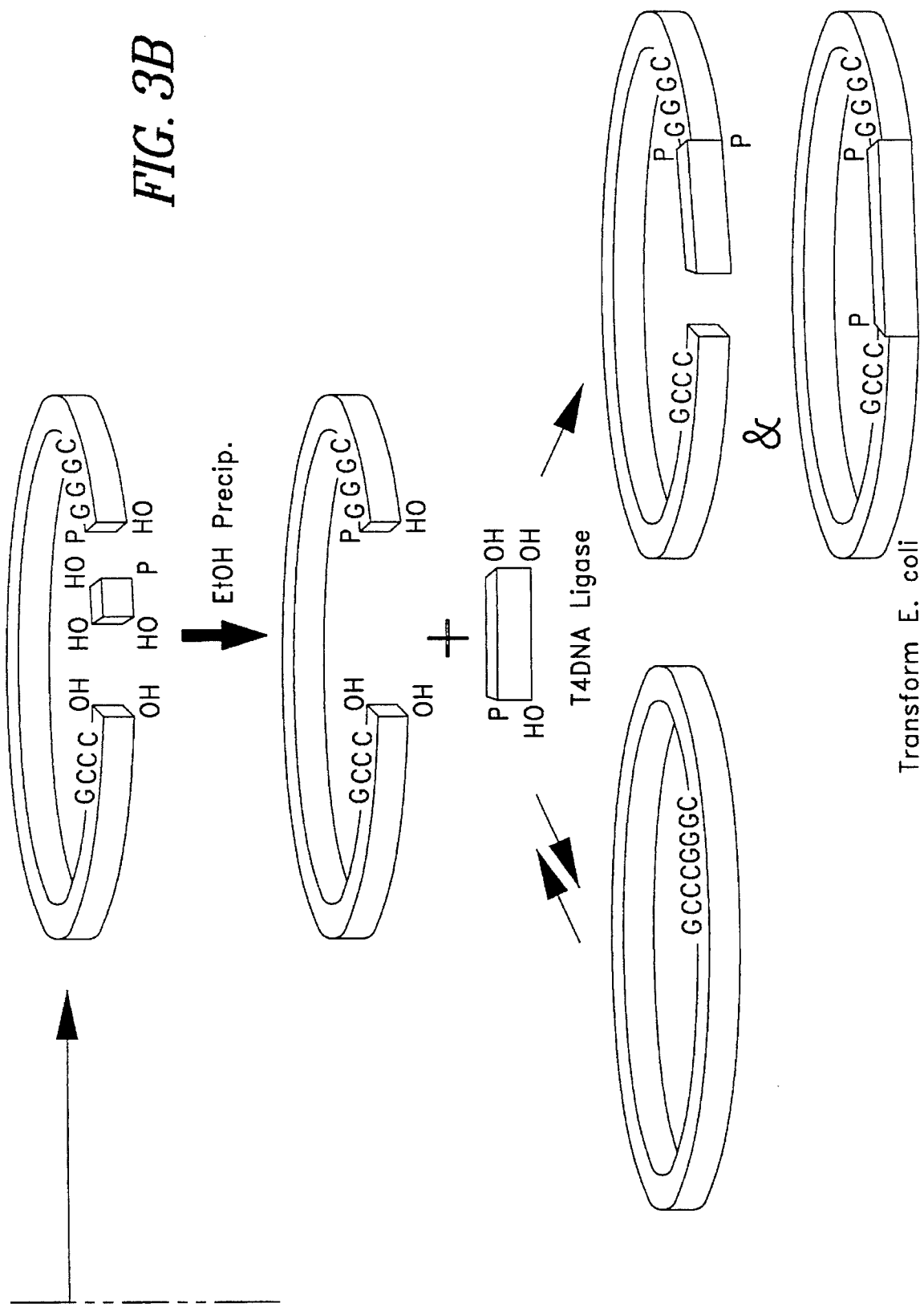

As shown in FIG. 2, plasmid pMW239 was designed to directionally clone monophosphorylated insert fragments. The restriction enzyme Srf I (5'-GCCC:GGGC-3') has the site for Sma I (5'-CCC:GGG-3') integrated in its target sequence. A multiple cloning site designed with the sequence 5'-GCCCGGGC-//-CCCGGGC- 3' (SEQ ID NO:13) contains a single Srf I site and two Sma I sites. Digestion with Srf I, followed by treatment with alkaline phosphatase yielded a dephosphorylated vector that, when digested with Sma I, recreated a Srf I site due to a C deoxynucleotide 3' to the Sma I site (see FIG. 2 and FIG. 3). The new Srf I site is uniterminally monophosphorylated at one side. Ligation of this vector created a nicked circle which is amenable to restriction by the Srf I endonuclease.

The cloning site in Srf I, CIAP, Sma I-treated pMW239 is bracketed by two octanucleotide-recognizing restriction enzymes, NotI (5'-GC:GGCCGC-3') and AscI (5'-GG:CGCGCC-3'), and three hexanucleotide recognizing restriction enzymes, SacI (5'-GAGCTC-3'), KpnI (5'-GGTACC-3') and NdeI (5'-CATATG-3').

For protein synthesis, the pMW239 vector contained a β-galactosidase promoter 5' to the insertion site, a T7 promoter, an *E. coli* ribosome binding site (RBS), and fMet start site 3' to the insertion site in the opposite direction. The β-galactosidase gene is functional and the reading frame of ligated Srf I, Sma I digested vector is conserved following ligation, allowing phenotypic color selection for insert-containing clones on Xgal plates. Protein fusions with the T7 RNA polymerase site will have an N-terminal methionine, proline fusion. The Nde I restriction site can be used to delete the two amino acids and fuse coding sequences directly to the fMet start site downstream from the RBS.

Figure 4:
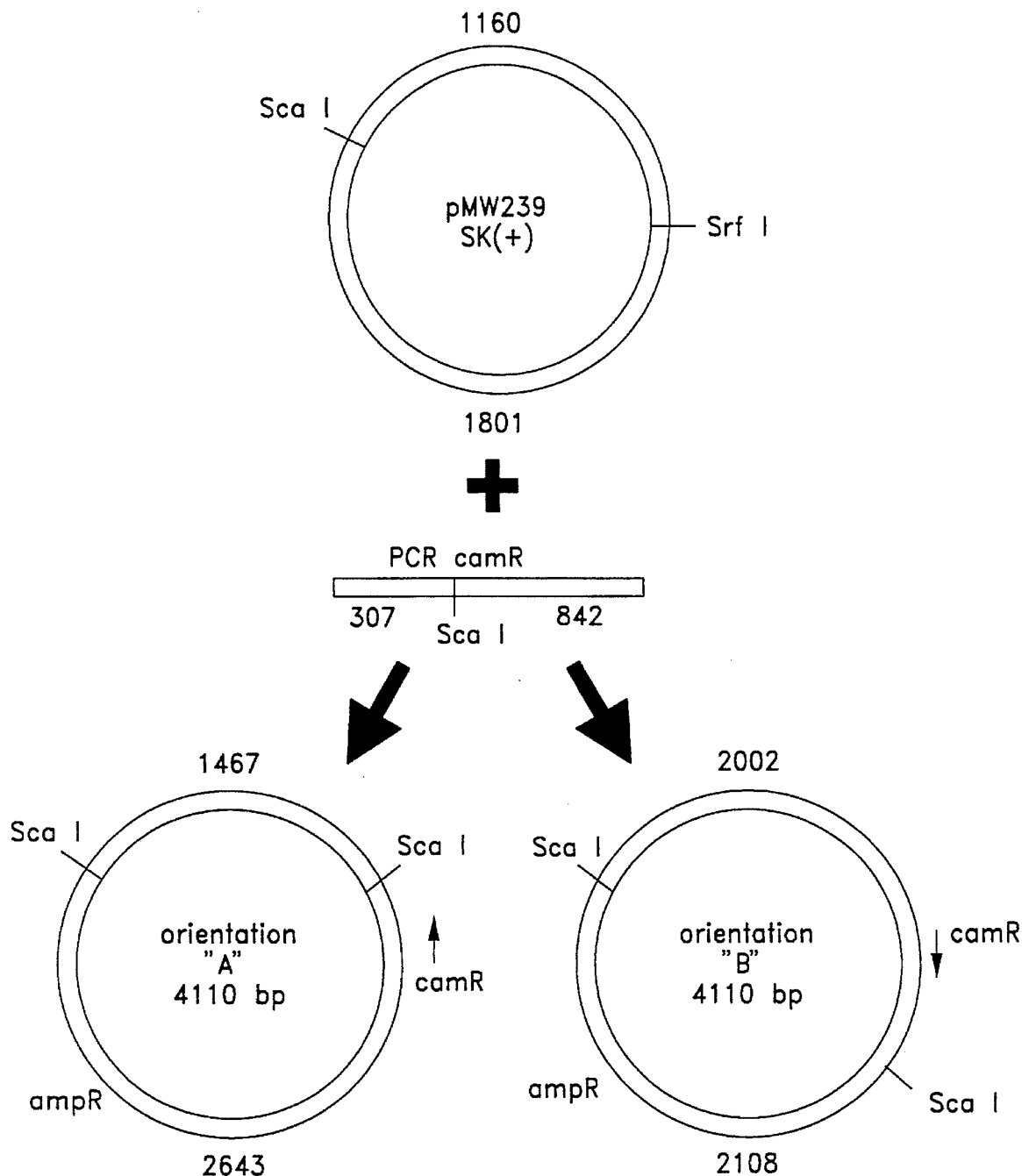
FIG. 4 is a diagram of possible cloned insert orientations. Confirmation of the method was performed on a PCR fragment of the camR gene having a single Sca I site. Orientations A and B would be expected to produce two different sets of fragments when digested with Sca I.

The pMW239 plasmid also contains a f1 origin for single-stranded DNA rescue and the ampicillin gene for transformant selection. Srf I only, and combinations of Srf I, CIAP, Sma I-treated pMW239 DNA were used to determine if monophosphorylated PCR insert could be cloned bi- and unidirectionally. A PCR product of the camR gene from restriction endonuclease-digested pBC was made with a primer set containing one phosphorylated primer (MW228). The PCR fragment was cloned into the two differently treated vectors and colonies containing the camR gene isolated. Twenty ampicillin, chloramphenicol-resistant colonies were chosen for analysis of clonal-insert orientation. Sca I restriction endonuclease was used to determine orientation (see FIG. 4). In one orientation "A" Sca I digestion would yield fragments of 1467 and 2643 bp. In the "B" orientation the fragments would be 2108 and 2002 bps.

Srf I-alone treated vector contained 40% (8 of 20) inserts in the "A" and 60% in the "B" orientation. The Srf I, CIAP, Sma I-treated pMW239 vector produced 5% (1 of 20) in orientation "A" and 95% (19 of 20) in orientation "B". This strongly supported our proposal of using monophosphorylation to directionally clone an insert DNA into a target vector.

A method is presented to directionally clone blunt-ended PCR fragments containing a single phosphorylated terminus. The PCR cloning vector is modified enzymatically using Srf I, CIAP, and Sma I. The ligation reaction is performed in the presence of both T4 DNA ligase and Srf I.

One skilled in the art will appreciate that one can use this procedure with other restriction enzymes in order to enzymatically create monophosphorylated vector DNA. Alternatively, it should be possible to ligate appropriate linkers containing modified 5' sites onto a suitable vector for either blunt, sticky or T/A type cloning. It should also be possible to use T4 DNA kinase to phosphorylate a PCR primer before the start of the reaction. The present invention advantageously provides a method for directionally cloning PCR fragments without any need to modify the primers with uracil or the addition of extra bases.

While a full and complete disclosure of a preferred embodiment of the present invention is set forth above, it is to be understood that various modifications, alternate constructions, and equivalent structures may be used without departing from the spirit of the present invention, and that the only limitations intended for the present invention are defined by the appended claims. For example, any method of using monophosphorylation to directionally clone an insert DNA into its target DNA is anticipated to be within the scope of the present invention.

I claim:

1. A method for directionally cloning an insert DNA sequence into a target DNA sequence comprising:
   generating a monophosphorylated target DNA sequence;
   generating a monophosphorylated insert DNA sequence; and
   combining said insert DNA sequence with said target sequence, wherein said insert sequence can ligate in only one orientation with respect to said target sequence.

2. The method of claim 1 wherein said target DNA sequence is a plasmid.

3. The method of claim 2 wherein said plasmid is an expression plasmid.

4. The method of claim 1 wherein said target DNA is lambda phage.

5. The method of claim 1 wherein said insert DNA is a PCR fragment.

6. The method of claim 1 wherein said combining step is a ligation with DNA ligase.

7. The method of claim 1 wherein said target sequence is produced using calf intestinal alkaline phosphatase (CIAP).

8. A method for directionally cloning a PCR generated DNA fragment into a target DNA comprising:
   generating a PCR fragment having only one phosphorylated 5' end;
   digesting a target DNA sequence with a blunt-end restriction enzyme;
   dephosphorylating the 5' ends of said target sequence;
   cleaving said target sequence to expose one 5' phosphate; and
   ligating said PCR generated DNA fragment with said target sequence, wherein said PCR generated DNA sequence can ligate in only one orientation with respect to said target sequence.

9. The method of claim 8 wherein said target DNA sequence is a plasmid.

10. The method of claim 9 wherein said plasmid is an expression plasmid.

11. The method of claim 8 wherein said target DNA is lambda phage.

12. The method of claim 8 wherein said dephosphorylating step uses calf intestinal alkaline phosphatase (CIAP).

13. The method of claim 8 wherein said blunt-end restriction enzyme is SrfI.

14. The method of claim 8 wherein said cleaving step uses Sma I.

15. The method of claim 8 wherein the generating step comprises PCR amplification of the insert DNA sequence by using one 5-phosphorylated primer and one unphosphorylated primer.

16. The method of claim 8 wherein the generating step comprises PCR amplification of the insert DNA sequence by using one DNA kinase-treated primer and one unphosphorylated primer.

* * * * *